United States Patent [19]

Adler

[11] Patent Number: 5,207,223
[45] Date of Patent: May 4, 1993

[54] APPARATUS FOR AND METHOD OF PERFORMING STEREOTAXIC SURGERY

[75] Inventor: John R. Adler, Stanford, Calif.
[73] Assignee: Accuray, Inc., Santa Clara, Calif.
[21] Appl. No.: 600,501
[22] Filed: Oct. 19, 1990
[51] Int. Cl.[5] ............................................. A61B 5/05
[52] U.S. Cl. .................................. 128/653.1; 606/130
[58] Field of Search ............... 606/130; 33/512, 514.1; 128/774, 662.05, 653.01; 378/205, 208, 204, 63–65

[56] References Cited

U.S. PATENT DOCUMENTS

| | | | |
|---|---|---|---|
| 4,118,631 | 10/1978 | Froggatt | 378/65 |
| 4,233,519 | 11/1980 | Coad | 378/65 |
| 4,448,268 | 3/1981 | Winter | 378/64 |
| 4,633,494 | 12/1986 | Klausz | 378/205 |
| 4,741,008 | 4/1988 | Franke | 128/24 EL |
| 4,791,934 | 12/1988 | Brunnett | 378/205 |
| 4,846,173 | 7/1989 | Davidson | 606/130 |
| 4,868,843 | 9/1989 | Nunan | 378/65 |

OTHER PUBLICATIONS

Cobalt-60 Teletherapy: A Compendium of International Practice, International Atomic Agency, Vienna, 1984; Montague Cohen & Joseph S. Mitchell.

*Primary Examiner*—William E. Kamm
*Assistant Examiner*—Samuel Gilbert
*Attorney, Agent, or Firm*—Ware & Freidenrich

[57] ABSTRACT

A method and an apparatus are set forth for selectively irradiating a target within a patient. A 3-dimensional mapping is provided of a mapping region surrounding the target. A beaming apparatus emits a collimated beam. Diagnostic beams at a known non-zero angle to one another pass through the mapping region. They produce images of projections within the mapping region. Electronic representations of the images are compared with the reference data thereby locating the target. The relative positions of the beaming apparatus and the living organism are adjusted in such a manner that the collimated beam is focused on the target region. The comparison is repeated at small time intervals and, when the comparison so indicates, the adjusting step is repeated, as needed, and in such a manner that the collimated beam remains focused on to the target region.

51 Claims, 4 Drawing Sheets

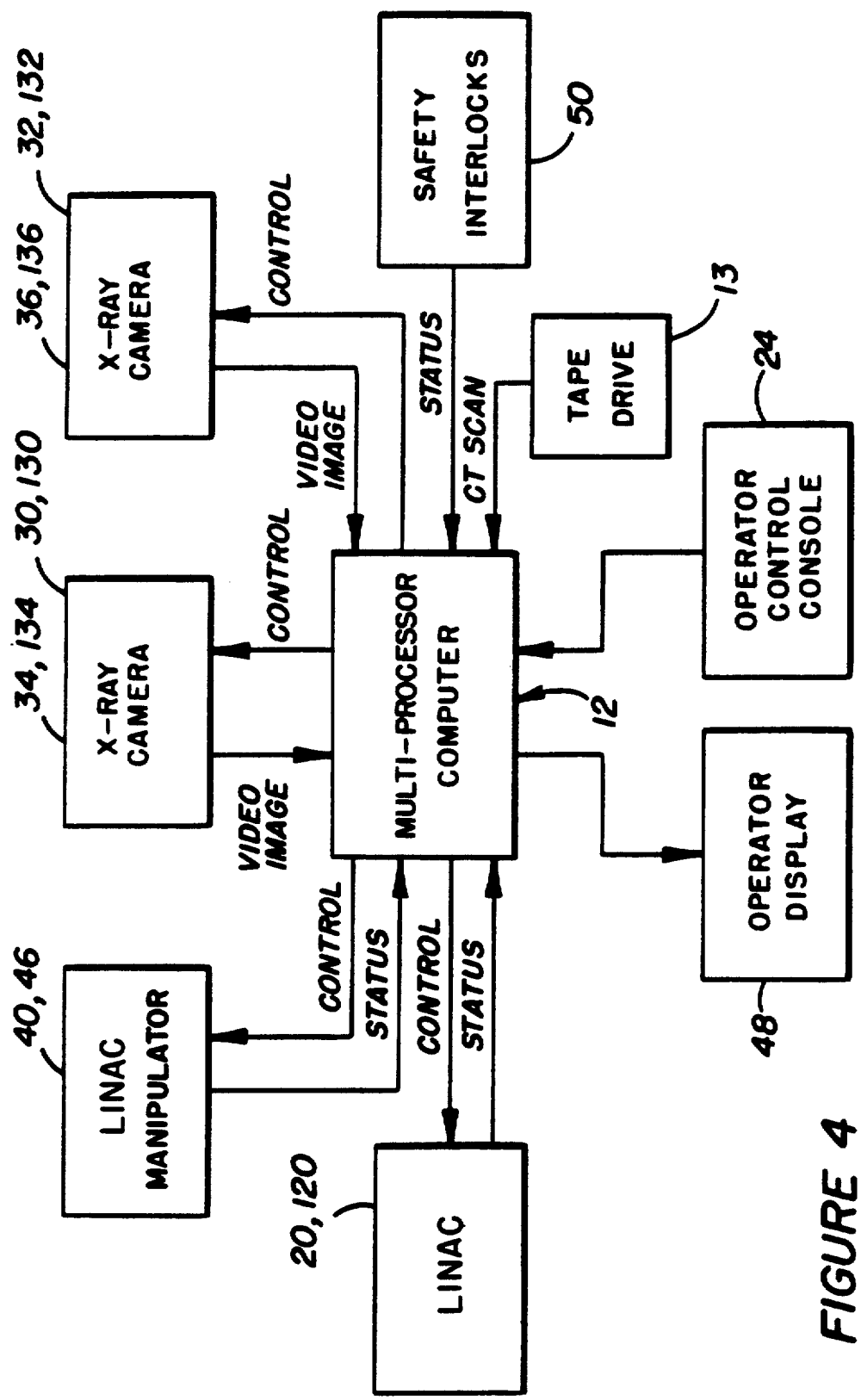
FIGURE 4   SYSTEM BLOCK DIAGRAM

APPARATUS FOR AND METHOD OF PERFORMING STEREOTAXIC SURGERY

TECHNICAL FIELD

The present invention relates to an apparatus and method for extending a surgical instrumentality to a target region in a patient, for example, for performing stereotaxic surgery, suitably using an x-ray linear accelerator. A collimated beam from the accelerator is used to cause tissue, for example tumorous tissue, to become necrotic. In another embodiment a biopsy probe can be extended to the target area. The invention is primarily concerned with assuring that the collimated beam, biopsy probe or other surgical instrumentality is properly aligned to extend to the tissue which is to be rendered necrotic, from which a sample is to be removed, or the like.

BACKGROUND OF THE INVENTION

The use of stereotaxic radiosurgery to render tissue, particularly tumorous tissue, necrotic is well known. In general, this technique has been utilized for brain surgery but has not been used for surgery elsewhere in a patient's body. The reason for the limitation to brain surgery is that if the beam is to be properly aimed or focused onto a target region which is to be rendered necrotic, it is necessary to provide an external radioopaque frame which is in a fixed position relative to the targeted region. The frame is precisely positionable in space and provides a reticle which can be observed by passing diagnostic x-ray beams through the frame and through a region of the body which includes the target region to be irradiated thereby allowing the position of the patient or of the beaming apparatus to be adjusted so that it is properly focused upon that region. Most portions of the body do not have available bone structure to which such a frame can be readily attached.

Stereotaxis is a branch of neurosurgery that utilizes spatial information provided by neuroradiologic studies to treat certain disorders of the central nervous system with great accuracy. Conventional stereotaxis, as mentioned above, uses an external frame anchored with screws to the patient's skull as a frame of reference for both localizing (by radiologic studies) and treating intracranial tumors and malformations. Stereotaxic radiosurgery builds on this concept by combining the precise localizing capabilities of stereotaxis with a high-energy radiation source. Over the past twenty years several independent groups have utilized radiosurgical techniques to treat a variety of brain disorders with single large fractions of radiation. In contrast to conventional radiation therapy (where the target tissue and the surrounding healthy tissue are substantially equally exposed to radiation and the healthy tissue is expected to have a higher resistance to radiation damage), the rationale behind such a procedure is that eventually radionecrosis will be produced at the targeted site. Because the outcome of this procedure is theoretically the same as standard resective surgery, the term radiosurgery was coined. The constantly growing list of indications for radiosurgical treatment includes arteriovenous malformations, acoustic neurinomas, metastatic lesions, unresectable skull base meningiomas, and several types of tumors involving the brain stem, pituitary and pineal region. Even Parkinson's disease and obsessive-compulsive disorders have been treated at the Karolinska Institute in Stockholm by creating well-circumscribed necrotic lesions in discrete brain locations. In many clinical situations stereotaxic radiosurgery is widely acknowledged as the treatment of choice.

The radiosurgical principle of confining radiation as much as possible only to the volume of a brain tumor is both a significant and timely concept. Meanwhile, the development of new technologies and the favorable clinical results that have been observed has lead to dramatic increases in the numbers of patients currently being treated with stereotaxic radiosurgery. Although exact figures are impossible to find at this point, reports in the literature and discussions with experts in the field of radiosurgery suggest that already several thousand patients per year, worldwide, are being treated with this technique. Despite such growing enthusiasm for stereotaxic radiosurgery, numerous theoretically attractive uses of such therapy remain impractical because of limitations in current instrumentation.

Although conventional stereotaxic radiosurgery combines a necrosing dose of energy largely to the lesion in question, there are limits to this capacity (regardless of radiation source) and inevitably normal brain is in some measure also irradiated. Overall, the smaller the volume of brain that is irradiated, the less the risk of healthy tissue radionecrosis. In the ideal situation, i.e., the treatment of very small volume lesions, normal tissue tolerance is not an issue for radiosurgeons. However, for both radiophysical and radiobiological reasons, radiosurgical treatment of the more frequently encountered larger lesions is problematic. With a risk that is proportional to both dose and the volume irradiated, radiation neorosis of the brain adjacent the treated lesion remains the major complication of stereotaxic radiosurgery. Consequently, despite the precision of stereotaxic radiosurgery, the normal tolerance to a large single dose of radiation is often a concern and strict attention must be paid to dose and volume parameters. This holds true for every radiosurgical technique regardless of radiation source.

The apparatus and method of the present invention have several advantages over other currently available radiosurgical systems. In particular, when operating in accordance with the present invention it is possible to perform multiple fraction radiosurgical treatment (separating the overall dose into a plurality of fractional doses and delivering the fractional doses hours or even days or weeks apart) utilizing the apparatus and method of the present invention. Consequently, a new type of ionizing radiation therapy is provided for brain tumors, one that blends conventional radiation therapy techniques with surgical principles of accurate anatomic localization. Presently there is no practical method for delivering multiple fraction precision radiation treatment to brain tumors because a frame must be left attached to the patient's skull with screws for the entire time of treatment which may desirably be weeks if one is attempting to minimize healthy tissue radioneorosis. In making precise multiple fraction therapy feasible, widespread application of the technique is possible in the treatment of the many tumors that are currently poorly treated with either surgery or radiation therapy.

The problems encountered in the radiosurgical treatment of the more frequently encountered larger lesions have provided much of the impetus for development of the present invention. Although the intent of the conventional stereotaxic radiosurgical treatment is to induce radionecrosis throughout the entire volume of a targeted tumor or malformation, one is limited by the above-described radiophysical and biological problems. Fractionated radiosurgery, which can be carried out using the apparatus and method of the present invention, is intended to accomplish the same objective, yet normal brain immediately adjacent to the tumor inherently receives a more tolerable dose and fraction. The total dose of radiation to the tumor can be pushed high enough to induce necrosis, yet still provide normal tissues, which received much less radiation, enough time for cell repair. Comparison between the cell kinetics of normal brain and the lesion being treated are only relevant as they pertain to this issue. It is critical to keep in mind that normal brain is relatively tolerant of even very high radiation doses delivered to small volumes. Furthermore, since in one reported instance a patient died from acute uncontrollable tumor and brain edema immediately following stereotaxic irradiation of a large tumor, there should be a benefit to inducing gradual neorosis in large tumors with fractionated therapy.

Despite the theoretical benefits of fractionated radiosurgical treatment, current techniques of stereotaxic localization precludes such an approach. Specifically, the major obstacle is a need for an external frame, attached to the patient's head with screws, which is impractical, if not impossible, to keep in place over the several days to few weeks needed to carry out such a therapy. Since the present invention does not rely on rigidly connected frames, it readily circumvents this problem. In addition, the computer mediated stereotaxic radiosurgery of the invention, with minor modifications, opens up the possibility of using radiosurgery outside the cranium, a thoroughly unexplored concept. Given the phenomenal development of new imaging techniques over the past fifteen years, there is now the means to visualize accurately nearly all body structures, and as a consequence, it seems reasonable that stereotaxic radiosurgical principles shall be of benefit in the treatment of non-brain neoplasms as well. Furthermore, since stereotaxic radiosurgery often provides a substitute for resective surgery, its utilization will lead to major savings for society.

As is apparent from the above discussion, it would be desirable to have a stereotaxic radiosurgical instrument which would be capable of use elsewhere than for brain surgery, which indeed could be used to excise non-tumorous tissue such as glands, if desired, which would operate with substantially no patient discomfort and which would make possible the convenient and safe use of doses of radiation accurately delivered in separate fractions, if need be, over a total elapsed time period of several day or weeks.

It is also desirable to be able to properly and accurately align other surgical instrumentation, e.g., a biopsy probe which can then be extended linearly into a patient up to a tumor or the like where sampling can be performed.

DISCLOSURE OF INVENTION

The present invention is directed to overcoming one or more of the problems as set forth above.

In accordance with an embodiment of the invention a method is set forth for selectively irradiating a target region within a living organism. The method comprises preparing a 3-dimensional mapping of at least a portion of the living organism, the mapping covering a mapping region which includes and is larger than the target region. The mapping is stored as reference data. The organism is positioned with the mapping region within the target area of a beaming apparatus which, when activated, emits a collimated surgical beam of a strength sufficient to cause the target region to become necrotic. First and second diagnostic beams are passed through the mapping region with the beams being at a known non-zero angle relative to one another. The beams are used to produce respective first and second images of respective first and second projections within the mapping region. Electronic images are produced which are representative of the first and second images. The electronic images are compared with the reference data to provide position data representative of the relative spatial locations of the collimated beam and of the target region. The relative positions of the beaming apparatus and the living organism are adjusted in such a manner that the collimated beam is focused on the target region. The comparison is repeated at small time intervals and, when the comparison so indicates, the adjusting step is repeated, as needed, and in such a manner that the collimated beam remains focused on to the target region.

In accordance with another embodiment of the present invention an apparatus is set forth for selectively irradiating a target region of living tissue within a living organism. The apparatus includes a data storage memory having stored therein a 3-dimensional mapping of at least a portion of a living organism, the mapping covering a mapping region which includes and is larger than the target region. A beaming apparatus is present which, when activated, is adapted to emit a collimated surgical beam of a strength sufficient to cause the target region to become necrotic. Means are provided for selectively activating the beaming apparatus. Means are provided for passing first and second diagnostic beams through the mapping region, the first and second diagnostic beams being at a known non-zero angle relative to one another, to produce respective first and second images of respective first and second projections within the mapping region. Means are provided for producing electronic images from and representative of the first and second images. Means are provided for comparing the 3-dimensional mapping stored in the data storage memory with the electronic images representative of the first and second images to derive therefrom data representative of the real time location of the target region. Means are provided for adjusting the relative positions of the beaming apparatus and the living organism as needed in response to the data representative of the real time location of the target region in such a manner that the collimated beam, when activated, is continuously focused on to the target region.

In accordance with yet another embodiment of the invention a method is set forth for selectively aligning a target region within a living organism with a linearly extendable surgical instrumentality. The method comprises preparing a 3-dimensional mapping of at least a portion of the living organism, the mapping covering a mapping region which includes and is larger than the target region. The mapping is stored as reference data. The organism is positioned with the mapping region within the target area of a surgical apparatus which, when activated, causes the linearly extendable surgical instrumentality to extend to the target region. First and second diagnostic beams are passed through the mapping region, the first and second diagnostic beams being at a known non-zero angle relative to one another, to produce respective first and second images of respective first and second projections within the mapping region. Electronic images are produced representative of the first and second images. The electronic images are compared with the reference data to provide position data representative of the relative spatial locations of the linearly extending surgical instrumentality and of the target region. The relative positions of the surgical apparatus and the living organism are adjusted in such a manner that the linearly extending surgical instrumentality is aimed at the target region.

In accordance with another embodiment still of the invention an apparatus is disclosed for selectively aligning a target region of living tissue within a living organism. The apparatus comprises a data storage memory having stored therein a 3-dimensional mapping of at least a portion of the living organism, the mapping covering a mapping region which includes and is larger than the target region. a surgical apparatus is provided which, when activated, is adapted to extend a linearly extendable surgical instrumentality to the target region. Means are provided for selectively activating the surgical apparatus. Means are provided for passing first and second diagnostic beams through the mapping region, the first and second diagnostic beams being at a known non-zero angle relative to one another, to produce respective first and second images of respective first and second projections within the mapping region. Means are provided for producing electronic images representative of the first and second images. Means are present for comparing the 3-dimensional mapping with the electronic images representative of the first and second images to derive therefrom data representative of the real time location of the target region. Means are provided for adjusting the relative positions of the surgical apparatus and the living organism in response to the data representative of the real time location of the target region in such a manner that the linearly extending surgical instrumentality, when activated, is aimed at the target region.

The apparatus and method set forth above have a number of advantages over prior art stereotaxic radiosurgical methods and apparatus. First of all, the need for an external frame is completely eliminated with the frame being replaced by the 3-dimensional mapping. Second, since it is not necessary to mount a frame to the patient's body, pain from such a frame is eliminated as is the possibility of infection. Third, stereotaxic radiosurgery can be utilized virtually anywhere in the patient's body. Fourth, stereotaxic radiosurgical procedures can be conveniently and accurately carried out in a fractionated manner over as long a period of time as desired, for example, over several days or weeks, if necessary or desirable.

BRIEF DESCRIPTION OF THE DRAWINGS

The invention will be better understood by reference to the figures of the drawings wherein like numbers denote like parts throughout and wherein:

FIG. 4 illustrates, schematically, a system block diagram in accordance with an embodiment of the present invention.

BEST MODE FOR CARRYING OUT INVENTION

Figure 1:
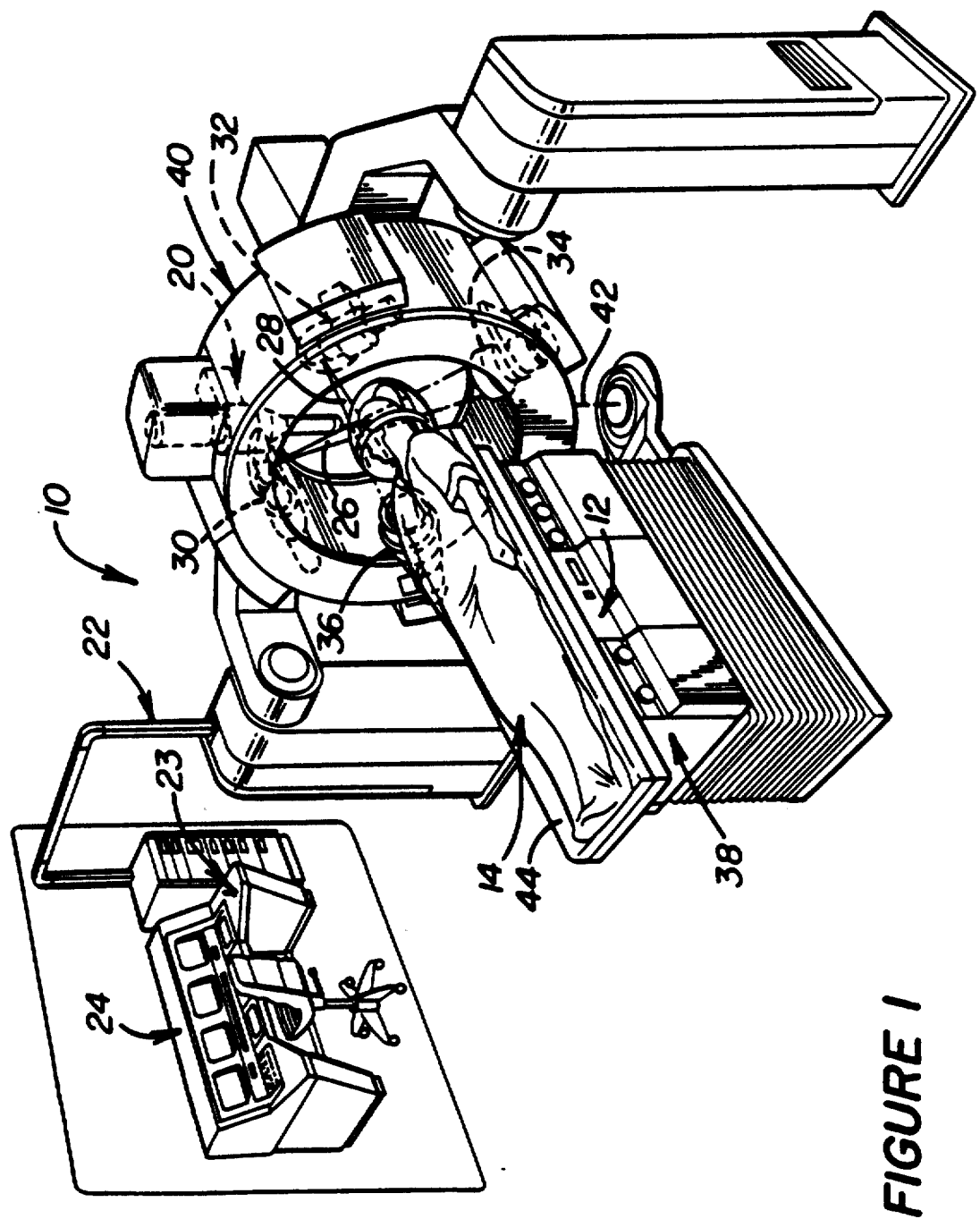
FIG. 1 illustrates, in isometric view, one embodiment of an apparatus in accordance with the present invention.

The present invention provides a stereotaxic radiosurgical apparatus 10, an embodiment of which is illustrated in FIG. 1.

Figure 2:
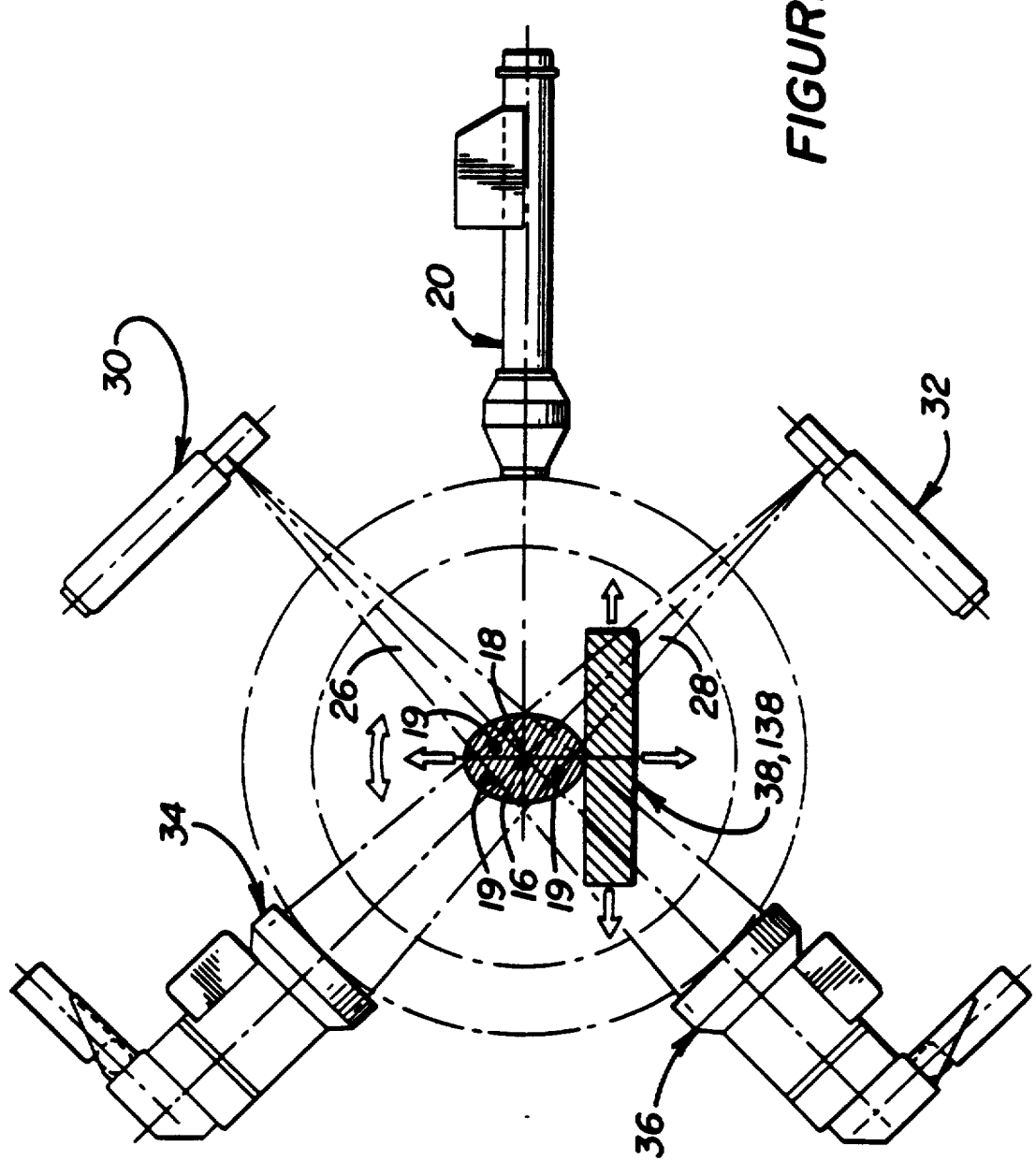
FIG. 2 illustrates, schematically, diagnostic x-ray imaging and accelerator focusing aspects of the present invention.

In accordance with the invention a data storage memory is provided. The data storage memory can be in a data processor 12, for example, a microprocessor 12 or in an auxiliary device such as a disc or tape storage unit 13 (FIG. 4). The microprocessor 12 or the storage unit 13 has stored therein a 3-dimensional mapping of at least a portion of a living organism, i.e., of a patient 14. If the storage unit 13 is present the 3-dimensional mapping data, normally in digital form, will generally be loaded into the microprocessor 12 for comparison purposes. The mapping covers a mapping region 16 (see FIG. 2) which includes and is larger than a target region 18 within the patient which is being selectively irradiated. The mapping region 16 of FIG. 2 is essentially the portion of the cranium 15 of the patient 14 so that bone structure is present to serve as an alignment reference. If desired, three or more fiducials 19 can be implanted, in which instance including bone structure as an alignment reference is not necessary. This could be done for treatments of the brain but could be particularly desirable or necessary in less bony areas of the body.

The 3-dimensional mapping can be obtained by conventional techniques. For example a CAT scan (CT) can be utilized to obtain this image or magnetic resonance imaging (MR) can be used to obtain this mapping. As is well known CT or computerized tomography operates through measurement of the differential absorption of x-ray beams and treats the resulting data by Fourier transforms. MR utilizes the nuclear magnetic resonance property to obtain a 3-dimensional mapping. Apparatus for carrying out both procedures is available commercially. Furthermore, the data is available in digitized form whereby it can be readily stored in the memory unit 13 and/or in the microprocessor 12.

A beaming apparatus 20 is provided which, when activated, emits a collimated surgical ionizing beam of a strength sufficient to cause the target region 18 to become necrotic. One beaming apparatus which can be utilized is in the nature of a linear accelerator, preferably an x-ray linear accelerator, although other ionizing radiation sources could be used as can other ionizing radiations. Such x-ray apparatus is available commercially. It has also been described in a number of texts including "The Physics Of Radiology", 3rd Edition, 5th printing, by A.E. Johns and J.R. Cunningham, 1974, Charles C. Thomas, publisher, Springfield, Illinois. A radio frequency wave is produced by a power supply, modulator and power tube and is fed into the accelerator 20 via a wave guide 22. The velocity of the wave increases as it passes down the tube.

Electrons can be given an energy of, for example, 6 Mev in a 2 meter long tube. The electrons can be impinged upon a target where x-rays are produced in a beam collimated in a desired direction. Such apparatus is available from various manufacturers including, for example, Varian. The preferred apparatus, an x-ray linear accelerator, preferred because of its relatively small size and relatively light weight, is manufactured by Sohonberg Radiation Corporation of Santa Clara, California and is marketed under the trademark MINAC.

On operator activation of a switch, for example a switch 23 on a control console 24, the beaming apparatus 20 can be activated.

In accordance with the invention and as illustrated in FIGS. 1 and 2, means are provided for passing first and second diagnostic beams 26 and 28 through the mapping region 16, the beams being laterally extensive sufficiently to provide projections of the mapping region. The first and second diagnostic beams 26 and 28 are at a known non-zero angle relative to one another. In the particular embodiment illustrated in FIGS. 1 and 2 the beams 26 and 28 are orthogonal to one another. However, any angle can be utilized so long as it is non-zero. Beams 26 and 28 are generated respectively by respective diagnostic x-ray generating apparatus 30 and 32. Image receivers 34 and 36, respectively, in the embodiment of FIGS. 1 and 2, image amplifiers, receive the beams 26 and 28 and pass the resulting electrical signals, with amplification if desired, to the microprocessor 12 where they are compared with the 3-dimensional mapping.

As is shown in FIG. 4, the image receivers 34 and 36 are connected to the microprocessor 12. The image receivers 34 and 36 can themselves provide digital signals or an A/D converter can be present as part of or in association with the microprocessor whereby images detected by the image receivers 34 and 36, which are representative of two different planar regions of the mapping region 16, can be compared in digital form with the 3-dimensional mapping (in digital form) of the mapping region 16. Utilizing conventional geometric calculation techniques the precise location of the target region 18 which is to be irradiated is thereby fully known.

Means are provided for adjusting the relative positions of the beaming apparatus 20 and the patient 14 as needed in response to data which is representative of the real time location of the target region 18 in such a manner that the collimated beam, when activated, is continuously focused on to the target region 18. In the particular embodiment illustrated in FIG. 1 the means for adjusting the relative positions of the beaming apparatus and the patient comprises a gantry 40 to which the beaming apparatus 20, the diagnostic x-ray generators 30 and 32 and the image receivers 34 and 36 are mounted along with conventional apparatus for lowering and raising the operating table 38 and for rotating it about an axis 42 and for tilting the top 44 of the operating table 38 about a longitudinally extending axis, all as illustrated by arrows in FIG. 2. The broad range of adjustment of the relative positions of the gantry 40 and the patient 14 allows the collimated beam to be continuously focused on the target region while the healthy tissue through which the collimated beam passes is changed, as by rotating the beaming apparatus 20 through as much as 360° about the patient. Previous apparatus was limited to about 180° rotation. Generally, it is preferable to keep the patient 14 relatively stationary and to move the gantry 40.

Figure 3:
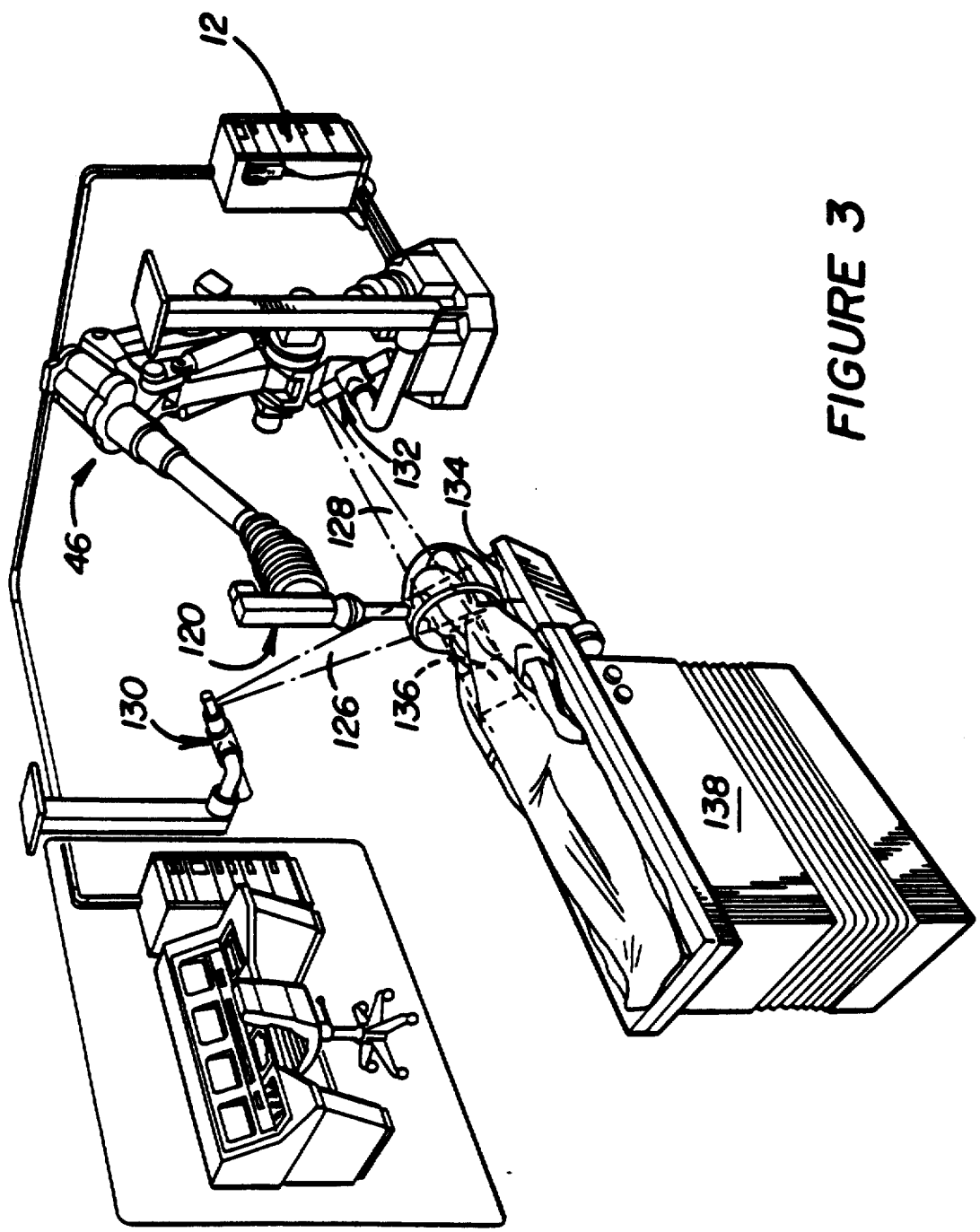
FIG. 3 illustrates, in a view similar to FIG. 1, an alternative embodiment of an apparatus in accordance with the present invention.

FIG. 3 illustrates an alternative embodiment of an apparatus in accordance with the present invention wherein the gantry 40 is eliminated as is the necessity to move the operating table 138.

In the embodiment of FIG. 3 the beaming apparatus 120 is supported and positioned by a processor controllable robotic arm mechanism 46 which has six axes of motion whereby the beaming apparatus 120 can be moved freely about the patients body, up or down, longitudinally along the patients body, or laterally along the patients body. Such robotic arm mechanisms are commercially available from, for example, GMF Robotics of Santa Fe Springs, California and are sold under the designation DS-420. Utilizing such an apparatus the collimated ionizing radiation can be targeted on the site of treatment i.e., the target region, from substantially any desired directions. Thus, this embodiment allows the collimated beam to pass for much less time through any particular region of healthy tissue than was the case with the prior art apparatus.

The means for passing first and second diagnostic beams 126 and 128 through the mapping region 18 in the FIG. 3 embodiment is in the nature of a pair of x-ray generators 130 and 132 which can be permanently mounted, for example, to the ceiling (not shown). Appropriate image receivers 134 and 136 serve to produce electronic images representative of the respective first and second images of the respective first and second projections within the mapping region 16 in the patient 14. The electronic images are passed to the microprocessor 12, going through an A/D converter if the images themselves are not already digital, whereat comparison can take place. Signals are then generated by the microprocessor 12 to control the positioning of the robotic arm mechanism 46 whereby the position of the beaming apparatus 120 is adjusted to assure that the collimated surgical beam which it produces is focused on the target region 18 which is being irradiated.

FIG. 4 illustrates, in system block diagram form, operation of the logic by which the apparatus of FIG. 1 or FIG. 3 can be controlled. The 3-dimensional mapping, which covers a mapping region 16, is stored, for example, on tape in tape drive 13. Signals from the image receivers 34,134 and 36,136 are passed to the processor 12. Control signals from the processor 12 are passed back to the image receivers 34,134 and 36,136 and/or to the diagnostic x-ray generating apparatus 30,130 and 32,132 to activate them at desired time intervals or at operator command, all as indicated in FIG. 4. Signals from the processor 12 are passed to the robotic arm mechanism 46 or to the gimbal 40 thus controlling its positioning with return signals from the gimbal 40 or robotic arm mechanism 46 indicative of positioning status being returned to the processor 12. The beaming apparatus 20,120 is normally activated by the processor 12 only when it is properly focused on the target region 18 and is normally otherwise not activated. However, it is possible to leave the beaming apparatus 20,120 on so long as exposure time of non-target regions in the patient 14 is sufficiently restricted so as to preclude radioneorosis of non-target tissue. The collimated beam can be retargeted on the target region from any selected direction thus providing the capability of irradiating from multiple directions. Operator controls are provided by the operator control console 24 which includes an operator display 48. Safety interlooks 50 are also provided for discontinuing operation of the processor 12 and of the beaming apparatus 20,120 in instances when such is necessary.

Basically, the image receivers 34,134 and 36,136 provide images which are separated in time by selected time intervals, these images are compared in the processor 12 with the CT scan which has generally been loaded into the processor 12 from the tape drive 13 and the positioning of the gantry 40 or robotic arm mechanism 46 is adjusted, as necessary, to retain focussing of the collimated beam generated by the beaming apparatus 20,120 upon the target region 18 within the mapping region 16 in the patient. The gimbal 40 or the robotic arm mechanism 46 can desirably be moved either continuously or in steps while the collimated beam is kept focused upon the target region 18, thus minimizing the extent to which any healthy tissue in the path of the beam is exposed to ionizing radiation.

In general it should be noted that apparatus and method of the present invention can be utilized substantially anywhere on the body. In those regions where there is no bone present to provide necessary markers from which the target region 18 can be located it may be necessary to insert the three fiducials 19 so as to provide artificial landmarks. It is also possible to use one or two fiducials if they are shaped to provide directional indications of their spatial orientation and/or if enough bone is present to provide one or more partial landmarks. The use of fiducials may even be desirable in locations in the body where sufficient bone is present since the fiducials may provide a better or more precise system for locating the target region 18 which is to be irradiated.

Furthermore, it should be recognized that a collimated beam is only one longitudinally extending surgical intrumentality which can be aligned and extended in accordance with embodiments of the present invention. For example, a biopsy probe or any other desired surgical instrumentality can be likewise aligned and used in accordance with the invention. Thus, the term linearly extending surgical instrumentality as used herein is meant to encompass all such instrumentalities and to cover solid instruments, beams, etc. so long as the instrumentality is useful for aa operative or diagnostic medical purpose.

The method of the invention will be generally understood from the above set forth description of the apparatus and its operation. It should be noted, additionally, that one can readily perform multiple fraction stereotaxic radiation treatments with a great degree of accuracy and with neither pain nor inconvenience to the patient 14. Thus, one can divide a desired dose of radiation into fractions, no one of which will overly exposed non-target tissue, and can administer these fractions of the total desired radiation dose, one at a time, over an extended period of time. It should also be noted that the treatment can include insertion of fiducials prior to mapping to aid in the accuracy of focusing of the collimated beam. Further, the method can be carried out on areas of the body where sufficient anchoring bone structure is not present to utilize an external reference frame.

INDUSTRIAL APPLICABILITY

The present invention provides an apparatus and method for irradiating a target region 18 within a patient 14. The apparatus and method are such that movement of the patient during treatment does not disturb the focusing of the x-ray beam which is being utilized. It is not necessary to attach an external frame to the body to provide a reticle whereby patient pain and dangers of infection are minimized. And, regions of the body other than the head can be readily treated utilizing the apparatus and method of the present invention.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

That which is claimed is:

1. A method for carrying out radiosurgery by selectively irradiating a target region within a living organism, comprising:
    preparing a 3-dimensional mapping of at least a portion of the living organism, the mapping covering a mapping region which includes and is larger than the target region;
    storing the mapping as reference data in digital form;
    positioning the organism with the mapping region within the target region of a radio-surgical beaming apparatus which, when activated, emits a collimated radiosurgical beam via a path through a mass of healthy tissue of a strength sufficient to cause the target region to become necrotic;
    passing first and second diagnostic beams, which are separate and distinct from the radiosurgical beam, through the mapping region substantially simultaneously, the first and second diagnostic beams being at a known non-zero angle relative to one another, to produce respective first and second images of respective first and second projections within the mapping region;
    producing first and second digital electronic images representative of the first and second images;
    digitally comparing the first and second electronic images with the reference data in digital form to provide position data representative of relative spatial locations of the collimated beam and of the target region, said first and second images being compared with said reference data sufficiently close in time after said images are produced by said first and second diagnostic beams such that said position data substantially represents real time spatial locations of the collimated beam and the target region relative to one another;
    in response to said real time spatial locations of said collimated beam and target region, adjusting the relative positions of the beaming apparatus and the living organism in such a manner that the collimated beam is focused onto the target region;
    activating the beaming apparatus and thereafter maintaining it in its activated state for the time necessary to provide a desired amount of irradiation;
    as radiosurgery is carried out, periodically repeating the comparing step at small time intervals using newly produced first and second images such that any movement of the target region relative to the focus of the collimated beam is detected in substantially real time; and
    repeating the adjusting step, as needed, to maintain the focus of the collimated beam on the target region.

2. A method as set forth in claim 1, wherein the repeating of the adjusting is carried out automatically in response to the position data obtained in the comparing step.

3. A method as set forth in claim 2, wherein the collimated surgical beam is an x-ray beam.

4. A method as set forth in claim 3, wherein the diagnostic beams are x-ray beams.

5. A method as set forth in claim 4, wherein the 3-dimensional mapping is prepared from a CAT scan procedure and is stored in digital form.

6. A method as set forth in claim 5, wherein the adjusting of the relative positions of the beaming apparatus and the living organism comprises moving the beaming apparatus while the living organism remains substantially stationary.

7. A method as set forth in claim 6, further including providing a selected total dose of irradiation by:
dividing the total dose into fractional doses;
utilizing the method of claim 6 to provide each fractional dose; and
supplying the fractional doses during time periods spaced apart in time from one another.

8. A method as set forth in claim 6, wherein the organism is part of a living body and wherein the target region is at a location in the body where sufficient bone structure is not present to mount an external reference frame.

9. A method as set forth in claim 6, further including, at some time prior to the mapping step:
implanting one or more fiducials in the mapping region.

10. A method as set forth in claim 1, wherein the collimated surgical beam is an x-ray beam.

11. A method as set forth in claim 10, wherein the diagnostic beams are x-ray beams.

12. A method as set forth in claim 11, wherein the 3-dimensional mapping is prepared from a CAT scan procedure and is stored in digital form.

13. A method as set forth in claim 12, wherein the adjusting of the relative positions of the beaming apparatus and the living organism comprises moving the beaming apparatus while the living organism remains substantially stationary.

14. A method as set forth in claim 13, further including providing a selected total dose of irradiation by:
dividing the total dose into fractional doses;
utilizing the method of claim 13 to provide each fractional dose; and
supplying the fractional doses during time periods spaced apart in time from one another.

15. A method as set forth in claim 13, wherein the organism is part of a living body and wherein the target region is at a location in the body where sufficient bone structure is not present to mount an external reference frame.

16. A method as set forth in claim 13, further including, at some time prior to the mapping step:
implanting one or more fiducials in the mapping region.

17. A method as set forth in claim 11, wherein the adjusting of the relative positions of the beaming apparatus and the living organism comprises moving the beaming apparatus while the living organism remains substantially stationary.

18. A method as set forth in claim 17, further including providing a selected total dose of irradiation by:
dividing the total dose into fractional doses;
utilizing the method of claim 17 to provide each fractional dose; and
supplying the fractional doses during time periods spaced apart in time from one another.

19. A method as set forth in claim 17, wherein the organism is part of a living body and wherein the target region is at a location in the body where sufficient bone structure is not present to mount an external reference frame.

20. A method as set forth in claim 17, further including, at some time prior to the mapping step:
implanting one or more fiducials in the mapping region.

21. A method as set forth in claim 1, wherein the diagnostic beams are x-ray beams.

22. A method as set forth in claim 21, wherein the 3-dimensional mapping is prepared from a CAT scan procedure and is stored in digital form.

23. A method as set forth in claim 22, wherein the adjusting of the relative positions of the beaming apparatus and the living organism comprises moving the beaming apparatus while the living organism remains substantially stationary.

24. A method as set forth in claim 1, wherein the adjusting of the relative positions of the beaming apparatus and the living organism comprises moving the beaming apparatus while the living organism remains substantially stationary.

25. A method as set forth in claim 1, further including providing a selected total dose of irradiation by:
dividing the total dose into fractional doses;
utilizing the method of claim 1 to provide each fractional dose; and
supplying the fractional doses during time periods spaced apart in time from one another.

26. A method as set forth in claim 1, wherein the organism is part of a living body and wherein the target region is at a location in the body where sufficient bone structure is not present to mount an external reference frame.

27. A method as set forth in claim 26, further including, at some time prior to the mapping step:
implanting one or more fiducials in the mapping region.

28. A method as set forth in claim 1, further including, at some time prior to the mapping step:
implanting one or more fiducials in the mapping region.

29. A method as set forth in claim 1, further including:
Repositioning the beaming apparatus such that, when activated, it emits the collimated beam such that the mapping region is within the target region and such that the collimated beam is directed via a different path through a different mass of healthy tissue to thereby minimize necrosis of healthy tissue; and
activating the beaming apparatus.

30. A method as set forth in claim 29, wherein the repositioning is within a plane and extends over an angle greater than 180°.

31. A method as set forth in claim 29, wherein the repositioning is over 3-dimensions.

32. A method as set forth in claim 1, further including:
periodically or continuously repositioning the beaming apparatus that emits the collimated beam in such a manner that the mapping region is within the target region and the collimated beam is periodically or continuously directed via different paths through different masses of healthy tissue to thereby minimize necrosis of healthy tissue.

33. A method as set forth in claim 32, wherein the repositioning is within a plane and extends over an angle greater than 180°.

34. A method according claim 1 wherein said radiosurgery is carried out on a human head without the use of a frame or any other external radiosurgery beam positioning reference.

35. A method according to claim 1 wherein said radiosurgical beaming apparatus includes a beam aiming member and wherein said apparatus is operated in a way which causes the aiming member to move continuously along a path transverse to the radiosurgical beam during radiosurgery.

36. A method according to claim 35 wherein said aiming member includes a gantry.

37. A method according to claim 35 wherein said aiming member includes a robotic arm.

38. An apparatus for carrying out radiosurgery by selectively irradiating a target region of living tissue within a living organism, comprising:
   a digital data storage memory having stored therein a 3-dimensional mapping of at least a portion of the living organism, the mapping covering a mapping region which includes and is larger than the target region;
   a beaming apparatus which, when activated, is adapted to emit a collimated radio surgical beam of a strength sufficient to cause the target region to become necrotic;
   means for selectively activating the beaming apparatus;
   means for passing first and second diagnostic beams, which are separate and distinct from said radiosurgical beam, through the mapping region substantially simultaneously, the first and second diagnostic beams being at a known non-zero angle relative to one another, to produce respective first and second images of respective first and second projections within the mapping region;
   means for producing first and second digital electronic images representative of the first and second images;
   means for digitally comparing the 3-dimensional mapping in digital form with the electronic images representative of the first and second images sufficiently close in time after said images are produced to derive therefrom data representative of a real time location of the target region; and
   means for adjusting the relative positions of the beaming apparatus and the living organism as needed due to any movement of the target region relative to the collimated beam in response to the data representative of the real time location of the target region in such a manner that the collimated beam, when activated, is continuously focused onto the target region.

39. An apparatus as set forth in claim 38, wherein the collimated surgical beam produced by the beaming apparatus is an x-ray beam.

40. An apparatus as set forth in claim 39, wherein the means for passing diagnostic beams through the mapping region passes x-ray beams through the mapping region.

41. An apparatus as set forth in claim 40, wherein the 3-dimensional mapping is prepared from a CAT scan procedure and is stored in digital form in the data storage memory.

42. An apparatus as set forth in claim 41, wherein the means for adjusting the relative positions of the beaming apparatus and the living organism moves the beaming apparatus while the living organism remains substantially stationary.

43. An apparatus as set forth in claim 38, wherein the 3-dimensional mapping is prepared from a CAT scan procedure and is stored in digital form in the data storage memory.

44. An apparatus as set forth in claim 43, wherein the means for producing electronic signals representative of the diagnostic beams produces such signals in digital form.

45. An apparatus as set forth in claim 44, wherein the means for adjusting the relative positions of the beaming apparatus and the living organism moves the beaming apparatus while the living organism remains substantially stationary.

46. A method for selectively aligning a target region within a living organism with a linearly extendable surgical instrumentality, comprising:
   preparing a 3-dimensional mapping of at least a portion of the living organism, the mapping covering a mapping region which includes and is larger than the target region;
   storing the mapping as reference data in digital form;
   positioning the organism with the mapping region within the target region of a surgical apparatus which, when activated, causes the linearly extendable surgical instrumentality to extend to the target region;
   substantially simultaneously passing first and second diagnostic beams, which are separate and distinct from said instrumentality, through the mapping region, the first and second diagnostic beams being at a known non-zero angle relative to one another, to produce respective first and second images of respective first and second projections within the mapping region;
   producing first and second electronic images representative of the first and second images;
   comparing the first and second electronic images with the reference data to provide 3-dimensional position data representative of the relative spatial locations of the linearly extending surgical instrumentality and of the target region, said first and second images being compared with said reference data sufficiently close in time after said images are produced by said first and second diagnostic beams such that said data represents substantially the real time locations of said instrumentality and the target region relative to one another; and
   adjusting the relative positions of the surgical apparatus and the living organism in such a manner that the linearly extending surgical instrumentality is aimed at the target region.

47. A method according to claim 46 wherein said instrumentality is a solid instrument such as a biopsy probe.

48. A method according to claim 46 wherein said instrumentality is a radiosurgical beam.

49. An apparatus for selectively aligning a target region of living tissue within a living organism with a linearly extendable surgical instrumentality, comprising:
   a data storage memory having stored therein a 3-dimensional mapping of at least a portion of the living organism, the mapping covering a mapping region which includes and is larger than the target region;

a surgical apparatus which, when activated, is adapted to extend a linearly extendable surgical instrumentality to the target region;

means for selectively activating the surgical apparatus;

means for substantially simultaneously passing first and second diagnostic beams, which are separate and distinct from said instrumentality, through the mapping region periodically, the first and second diagnostic beams being at a known non-zero angle relative to one another, to produce periodically pairs of respective first and second images of respective pairs of first and second projections within the mapping region;

means for producing first and second digital electronic images representative of the first and second images;

means for comparing the 3-dimensional mapping in digital form with the first and second digital electronic images representative of the first and second images sufficiently close in time after said images are produced to derive therefrom data representative of a 3-dimensional real time location of the target region; and means for adjusting relative positions of the surgical apparatus and the living organism in response to the data representative of the 3-dimensional real time location of the target region in such a manner that the linearly extending surgical instrumentality, when activated, is aimed at the target region.

50. A method for carrying out radiosurgery by selectively irradiating a target region within a living organism, comprising:

preparing a 3-dimensional mapping of at least a portion of the living organism, the mapping covering a mapping region which includes and is larger than the target region;

storing the mapping as reference data;

positioning the organism with the mapping region within the target region of a radiosurgical beaming apparatus which, when activated, emits a collimated radiosurgical beam from a beam aiming member forming part of the apparatus via a path through a mass of healthy tissue of a strength sufficient to cause the target region to become necrotic, said apparatus being operated in a way which causes said aiming member to move continuously along a path transverse to the beam during radiosurgery;

during movement of said aiming member, passing first and second diagnostic beams, which are separate and distinct from the radiosurgical beam, through the mapping region substantially simultaneously, the first and second diagnostic beams being at a known non-zero angle relative to one another, to produce respective first and second images of respective first and second projections within the mapping region;

producing first and second digital electronic images representative of the first and second images;

digitally comparing the first and second electronic images with the reference data in digital form to provide position data representative of relative spatial locations of the collimated beam and of the target region, said first and second images being compared with said reference data sufficiently close in time after said images are produced by said first and second diagnostic beams such that said position data substantially represents real time spatial locations of the collimated beam and the target region relative to one another;

in response to said real time spatial locations of said collimated beam and target region, adjusting the relative positions of the beaming apparatus and the living organism in such a manner that the collimated beam is focused onto the target region;

activating the beaming apparatus and thereafter maintaining it in its activated state for the time necessary to provide a desired amount of irradiation;

as radiosurgery is carried out, periodically repeating the comparing step at small time intervals during movement of said aiming member using newly produced first and second images such that any movement of the target region relative to the focus of the collimated beam is detected in substantially real time; and repeating the adjusting step, as needed, to maintain the focus of the collimated beam on the target region.

51. A method according to claim 50 wherein said radiosurgery is carried out on a human head without the use of a frame or any other external radiosurgery beam positioning reference.

* * * * *

UNITED STATES PATENT AND TRADEMARK OFFICE
Certificate

Patent No. 5,207,223

Patented: May 4, 1993

On petition requesting issuance of a certificate for correction of inventorship pursuant to 35 U.S.C. 256, it has been found that the above identified patent, through error and without deceptive intent, improperly sets forth the inventorship.

Accordingly, it is hereby certified that the correct inventorship of this patent is: John R. Alder, Stanford, CA; Russell Schonberg, Los Altos Hills, CA; and Peter Schonberg, Holualooa, Hawaii.

Signed and Sealed this Ninth Day of April 2002.

KEVIN P. SHAVER
*Supervisory Patent Examiner*
Art Unit 3736

UNITED STATES PATENT AND TRADEMARK OFFICE
Certificate

Patent No. 5,207,223                                                       Patented: May 4, 1993

On petition requesting issuance of a certificate for correction of inventorship pursuant to 35 U.S.C. 256, it has been found that the above identified patent, through error and without deceptive intent, improperly sets forth the inventorship.

Accordingly, it is hereby certified that the correct inventorship of this patent is: John R. Adler, Stanford, CA; Russell Schonberg, Los Altos Hills, CA; and Peter Schonberg, Holualooa, Hawaii.

This Certificate supersedes Certificate issued April 9, 2002.

Signed and Sealed this Tenth Day of September 2002.

KEVIN P. SHAVER
*Supervisory Patent Examiner*
Art Unit 3736